United States Patent [19]

Nielsen

[11] Patent Number: 4,828,553
[45] Date of Patent: May 9, 1989

[54] ANNULAR COUPLING SYSTEM FOR OSTOMY EQUIPMENT

[75] Inventor: Per Nielsen, Copenhagen, Denmark
[73] Assignee: Coloplast A/S, Denmark
[21] Appl. No.: 867,523
[22] Filed: May 27, 1986
[51] Int. Cl.⁴ ............................................. A61F 5/44
[52] U.S. Cl. .................................................. 604/339
[58] Field of Search ............................. 604/332–345, 604/337–345; 220/306

[56] References Cited

U.S. PATENT DOCUMENTS

| | | | |
|---|---|---|---|
| 3,077,284 | 2/1963 | McLaughlin | 220/306 |
| 3,528,420 | 9/1970 | Nielsen et al. | 604/342 |
| 4,359,051 | 11/1982 | Oczkowski | 604/339 |
| 4,610,676 | 9/1986 | Schneider et al. | 604/339 |
| 4,610,677 | 9/1986 | Mohiuddin | 604/341 |

Primary Examiner—John D. Yasko
Assistant Examiner—J. L. Kruter
Attorney, Agent, or Firm—Ostrolenk, Faber, Gerb & Soffen

[57] ABSTRACT

An ostomy equipment is described which comprises in combination a flat bandage to be adhesively affixed to the wearer's abdomen around an intestinal opening, an ostomy bag and two-part ring coupling to releasably attach the bag to the bandage. The two annular members of the ring coupling have co-operating annular profile components to ensure tightening, and co-operating annular projections with annular engaging faces substantially parallel with the bandage to counteract unintentional release. The connection between the bag and its annular coupling member is situated in its entirety radially within the co-operating engaging faces of the annular coupling members; this is a safeguard against leakage in case of a one-sided pull in the bag. The annular coupling member of the ring coupling is adapted to co-operate with an ostomy rod adapted to be placed under a bowel loop in case of transversal loop ostomy. For this purpose the ostomy rod has bevelled end faces to form oblique faces converging towards the under side of the rod, the oblique faces cooperating with a radially inwardly situated frusto-conical surface on the annular coupling member connected to the bandage. This enables positioning and change of the bandage without removing the ostomy rod from under the bowel loop.

6 Claims, 6 Drawing Sheets

Fig. 16
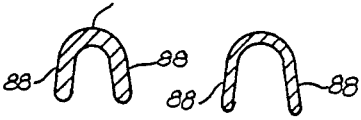
Fig. 17   Fig. 18
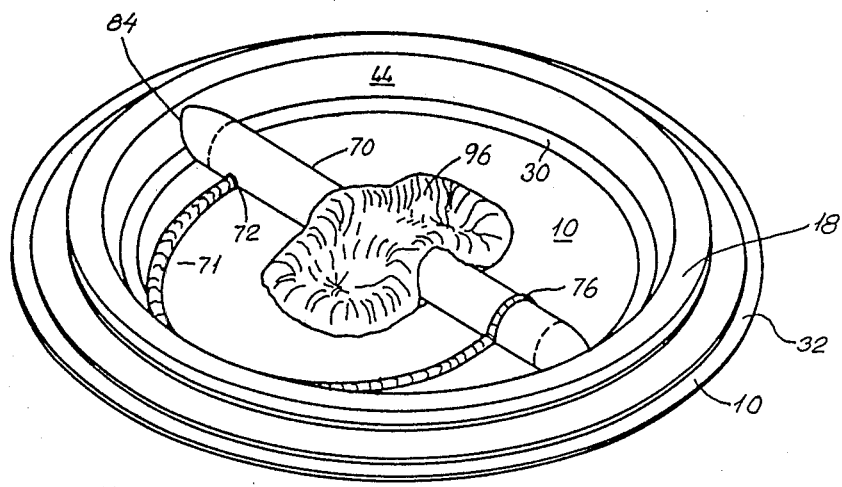
Fig. 19

ANNULAR COUPLING SYSTEM FOR OSTOMY EQUIPMENT

FIELD OF THE INVENTION

The present invention relates to an ostomy equipment comprising a substantially flat bandage to be adhesively affixed to the wearer's abdomen around an artificial intestinal opening flush with an opening in the bandage; an ostomy bag to receive fecal material from the intestine; a two-part coupling ring to releasably attach the bag to the bandage, the coupling ring consisting of two annular profiled members one of which is firmly connected to the bandage and the other to the bag, the two annular members comprising co-operating profile components to enable the coupling in its coupled state to tighten against the escape of gases, liquids and solids from the intestine and bag, and also comprising cooperating annular projections to counteract unintentional release of the coupled state of the two members; and optionally an ostomy rod adapted to be placed under a bowel loop projecting from the intestinal opening.

BACKGROUND OF THE INVENTION

A lot of systems of this kind are known. In many known coupling ring systems for ostomy equipment one of the annular members is provided with one or more substantially axial slots and the other with axial projections co-operating therewith. The details of such systems may vary much, but in all embodiments the grooves and projections are provided with co-operating tightening surfaces and frequently also with co-operating annular beads and sometimes also grooves resisting release of the two ring members from each other. Examples of such systems may be seen in, e.g., DE patent specification No. 1 105 558 and GB specifications Nos. 1 099 455, 1 571 657, 1 586 823, 1 586 824 and 1 583 027.

It has been found that the co-operating holding surfaces extending substantially in the axial directions of the annular member do not always adequately ensure against release of the coupled state at unintentional pull of the bag occurs, even if such pull is moderate and fairly evenly distributed over the perimeter of the ring coupling. When the bag is filled, it may itself cause a one-sided, oblique pull on a limited part of the ring and this may cause a local leakage in the coupling, possibly resulting in escape of intestinal gases accumulated in the bag and sometimes also liquid.

The unintentional release of the ring coupling upon a fairly uniform pull is avoided in a construction known from U.S. Pat. No. 4,078,567 (the purpose of which, incidentally, is another) wherein that the coupling member adapted to engage the abdomen of the patient is provided with an annular groove with a radially outwardly situated opening, and wherein that the edge of the opening in the bag through which the fecal material enters the bag, is connected with a solid annular coupling portion the cross section of which is approximately circular (in the specification called an O-ring) with a diameter as the axial width of the groove whereby it causes tightening when introduced into the groove; the wall of the groove farthest away from the abdominal wall of the patient and approximately parallel therewith effectively safeguards against unintentional release of the coupling at a uniform pull. The circular ring profile is connected with the bag, by means of a flat plate or disc extending radially outwardly relative to the O-ring. Accordingly, the engagement between the two annular coupling members is radial in contradistinction to the aforementioned axial engagements. The construction will not safeguard against local leakage a local pull on the bag at a limited part of the perimeter.

It is one object of the invention to avoid those drawbacks.

As mentioned, the ostomy equipment may optionally comprise an ostomy rod. In some cases of ostomy operations, e.g. when it is expected that the parts of the intestine downstream of the ostomy may later re-enter into its normal function, a loop of the intestine (bowel loop) is pulled outside the abdominal wall after the surgical opening thereof, a so-called transverse loop colostomy. Thereupon the loop is opened and sometimes its walls are sutured to the skin around the ostomy opening. Whether or not the bowel loop is sutured it is necessary during the initial period, normally 1-2 weeks, after the surgical operation, to support it mechanically to prevent, it from sliding back into the abdominal cavity or tearing the suture. An ostomy rod is used for this purpose. Originally there was used a glass rod which was placed under the bowel loop and with its ends abutting on the abdominal wall, outside the opening therein and under a bandage; often the rod was sutured to the skin. For many years ostomy rods have been made of plastics and moreover it has for many years been practice to place a bandage, frequently combined with a holding device for a bag for collecting fecal material, around the opening in the abdominal wall and under the ostomy rod, between the rod and the skin. It is normally necessary to replace the bandage once or a few times before the rod can be dispensed of, and it also has to be replaced if leakages occur so as to cause contact between intestinal waste and the skin.

Various forms of ostomy rods are known and commercially available. Claire Beresford describes in "Management of temporary colostomy", Nurse Times, 1981, 2:77, pp. 108-112, a rather rigid rod of circular cross section and provided with a short, stationary crossbar in one end and a corresponding, yet revolving crossbar in the other. When inserting and removing the rod into and from the position under the bowel loop the revolving crossbar is parallel with the rod but in the holding position perpendicular thereto; the crossbars serve for distributing the pressure on the abdominal wall and preventing the rod from sliding away from the holding position.

From DK patent specification No. 123689, which is equivalent to U.S. Pat. No. 2,483,868 to Marsan et al., there is known a colostomy equipment comprising a holding means for an ostomy bag. The holding means has a flange adapted to be secured to the abdomen of the patient around the artificial opening through which a transverse colostomy is projecting, and a ring projecting from the flange. The ostomy rod is adapted to be maintained in position with its ends in an internal annular groove in the ring. In order to be maintained in position in the internal annular groove, the end parts of the rod may be thinner than the remainder of the rod (which according to the drawing of the patent is cylindrical). In order to introduce the ends of the rod into the groove in the ring the latter is provided with at least two axial grooves, diametrically opposite each other, directed towards the annular groove either from the end of the ring adjacent the flange or the opposite end.

To place the equipment in position on the patient, the rod is inserted into one end of a flexible tube. The ends of the latter are conveyed through the central opening of the annular holding means. This is of the type where the axial grooves extend to the end of the ring farthest away from the flange and is guided over the bowel loop to place its flange so as to bear against the skin. Thereafter the flexible tube is pulled through (under) the bowel loop until the rod is so situated that approximately equal lengths thereof are visible on each side of the intestine. The tube is removed and the ends of the rod placed in the axial grooves. Finally the ring is turned round (about its axis) to be held securely in the internal annular groove. The possibility of turning the rod relative to the ring is strongly limited by its position perpendicular to the bowel loop. If the holding ring with its flange is combined with a bandage, which has been the practice for many years, it is almost impossible to revolve it because the bandage must be firmly connected to the ring and must also be adhesively affixed to the skin, in order to avoid leakage in the equipment and to avoid that intestinal fluid comes into contact with the skin.

Thus, the relative rotation of rod and ring causes big problems, and moreover it is necessary to ensure a very precise position of the ring relative to the rod before introducing the ends of the rod into the axial grooves, both with respect to the angular orientation of the rod relative to the ring and with respect to the position of the rod in its own longitudinal direction.

It is a further object of the invention to avoid these drawbacks. The said objects and further objects of the invention will be clear from the following description of the preferred embodiments of the invention.

SUMMARY OF THE INVENTION

One preferred embodiment of the ostomy equipment according to the invention comprises in combination
- (a) a substantially flat bandage adapted to be adhesively affixed to the wearer's abdomen around an intestinal opening flush with an opening in the bandage,
- (b) an ostomy bag adapted to receive fecal material from the intestine, and
- (c) a two-part ring coupling adapted to releasably attach the ostomy bag to the bandage, the ring coupling consisting of
  - (i) an annular, profiled first coupling member firmly connected to the bandage via at least one flat, annular flange situated around the opening in the bandage, said first coupling member projecting axially from the flange, and
  - (ii) an annular, profiled second coupling member firmly connected to the bag, the profiles of the two annular coupling members having
- ($\alpha$) co-operating annular profile components which in the coupled state of the two annular members tighten against the escape of gases, liquids and solids from the bag and the intestine, and
- ($\beta$) co-operating annular projections with annular engaging faces which are substantially parallel with the flange and adapted to counteract unintentional release of the coupled state of the two coupling members, and the improvement therein consists in that the connection between the bag and the second coupling member in its entirety is situated radially within the cooperating flange-parallel engaging faces.

The engaging faces substantially parallel with the flange—and hence with the bandage—ensure well against unintentional release of the coupled state of the coupling when the pull therein is fairly even, and are made with such a width and of such material that the intentional release will not cause difficulties.

Positioning the connection between the bag and the second coupling member—hereinafter also called bag coupling—radially inside the tightening and engaging faces ensure that a one-sided pull in the bag at a normally occurring strength, as may for instance occur when the bag is filled with fecal material, will not cause local leaking of the tightening connection but rather, at suitable construction of the tightening and engaging faces, improve the tightening and engagement.

Preferably, the second coupling member adjacent the bag has an annular, radially inwardly directed projection to which the bag is affixed at an annular connecting surface which in its entirety is situated radially within the co-operating tightening profile components and the co-operating engaging faces.

The annular projection to which the bag is affixed preferably is substantially wider, measured radially, then the engaging faces on the co-operating projections.

The projection of the first annular coupling member co-operating with the projection of the second annular member may according to the invention extend radially outwardly relative to a body portion of said first annular member and the corresponding projection of the second annular coupling member extend radially inwardly relative to a body portion thereof, whereas the projection of said first annular coupling member radially outermost may be provided with an annular projecting rim adapted to tightening engagement in the angle between the radially inwardly extending projection of the second coupling member and its body portion.

The second main embodiment of the invention is very similar to the first one so far as the bandage, the bag and the two-part coupling ring are concerned, but it furthermore comprises an ostomy rod; in other words, it comprises in combination
- (a) a substantially flat bandage adapted to be adhesively affixed to the wearer's abdomen around a surgically formed opening in the abdominal wall through which a loop of the intestine is projecting outside the abdominal wall and through an opening in the bandage,
- (b) an ostomy bag adapted to receive fecal material from the intestine,
- (c) a two-part ring coupling adapted to releasably attach the ostomy bag to the bandage, the ring coupling consisting of
  - (i) an annular, profiled first coupling member firmly connected to the bandage via at least one flat, annular flange situated around the opening in the bandage, said first coupling member projecting axially from the flange, and
  - (ii) an annular, profiled second coupling member firmly connected to the bag, the profiles of the two annular members having cooperating profile components to tighten against the escape of gases, liquids and solids from the bag and the intestine, and co-operating faces to counteract unintentional release of the coupled state of the two coupling members, and (d) an ostomy rod adapted to be placed under the loop of the intestine to maintain it in position outside the abdominal wall, and in this embodiment the improvement consists in that the ends of the ostomy rod are bevelled so as to form oblique faces converging toward the side of the rod adapted to face the bandage, and that the part of the first coupling member which projects from the flange(s) at its radially inner side has a frusto-conical surface having its smallest diameter adjacent the bandage and adapted to co-operate with the oblique faces of the rod.

Since the frusto-conical surface is identical over the entire perimeter, the angular position of the rod relative thereto has no importance and consequently the angular position of the rod during insertion is unimportant and pivotal movement thereof has no meaning. Moreover, the oblique end faces of the rod can to some degree slide axially on the conical surface whereby small inaccuracies in the position of the rod relative to its longitudinal direction may be settled by such sliding movement.

The oblique end faces of the rod may be parts of a conical surface congruent with the frusto-conical surface of the first annular coupling member, but many plastic materials used for the various parts in that case will cause a too big friction to ensure longitudianl adjustment of the position of the rod by sliding on the frustoconical surface, for which reason it is preferred that the oblique end faces of the rod are planar. Preferably the angle between the oblique faces of the rod and the under side thereof (i.e. that facing the bandage and the flange) is 105°–130°, especially preferred about 120° and the top angle of the conical surface of which the frusto-conical surface of the ring forms part, correspondingly 50°–75°, preferably about 60°. If the angle between the oblique faces and the under side of the rod is smaller (and the top angle bigger), the clearance to allow the longitudinal displacement of the rod becomes too small, and in the opposite case the relative sliding of the surfaces becomes difficult.

It will be understood that the radially inwardly situated frusto-conical surface of the first annular coupling member does not at all interfere with the radially outwardly situated faces adapted to co-operate with the corresponding faces on the bag coupling. In other words, it does not hamper the easy removal of a filled bag and its replacement with a new one.

An ostomy rod for use in this equipment of course must have its end faces bevelled so as to form oblique surfaces converging towards the under side of the rod; and the rod must have a length such that the distance between the oblique end faces, measured at the under side of the rod, is smaller than the largest diameter and bigger than the greatest diameter of the frusto-conical surface. Apart from this, the rod may be constructed in a lot of different ways. It may be solid, hollow (tubular) or have a U-shaped cross-section.

It is a disadvantage inherent in known ostomy rods that they are rigid and therefore cause difficulties when positioning and replacing the bandage around the ostomy opening in the abdominal wall. Usually the opening in the bandage has in so far as possible exactly the same size and shape as the ostomy opening and consequently the ostomy rod is much longer than the diameter of the opening in the bandage. When positioning or removing the bandage it is therefore necessary with known constructions to manipulate the rod longitudionally in a reciprocating manner to get it through the opening of the bandage in its entire length. This is troublesome and may cause pain because it takes place at a time where the surgical wounds are still fresh or at most a few weeks old. It also involves a risk of infection, and moreover it is important to avoid contact between the skin and intestinal matter since this can be very aggressive because of the enzymes contained therein.

It is a still further object of the invention to eliminate this drawback. This is achieved when the rod is elastically bendable in the direction away from its under side in one or two zones symmetrically placed with respect to the transversal middle plane of the rod.

DETAILED DESCRIPTION OF THE VARIOUS EMBODIMENTS OF THE INVENTION

Figure 1:
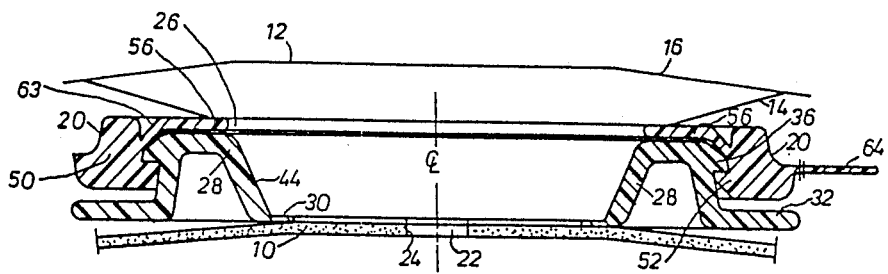
FIG. 1 is a diametrical cross section of a preferred embodiment of the equipment of the invention, with the two annular coupling members in the coupled state, FIG. 2 a section in larger scale, the parts likewise in the coupled state, FIG. 3 a cross-section corresponding to FIG. 1, but showing the effect of a one-sided pull of the bag, FIG. 4 a perspective view, with a portion cut away to show a cross-section, of another embodiment of the coupling, FIG. 5 a perspective view of an ostomy rod for use in connection with a two-part coupling ring as shown in FIGS. 1–4, FIG. 6 a longitudinal section of a part of the ostomy rod shown in FIG. 5, in co-operation with a first annular member shown in cross-section, of the kind illustrated in FIGS. 1–3, FIG. 7 a longitudinal section of the two ends of the rod and diametrically opposite parts of the annular member during insertion of the rod, FIG. 8 a perspective view of another embodiment of the ostomy rod, FIG. 9 the embodiment of FIG. 8 seen partly from the side, partly in longitudinal section of the middle plane perpendicular to the lower surface of the rod, the ring coupling also shown in cross-section at the left end of the figure and its first annular member at its right end, FIGS. 10–12 cross sections of the rod of FIGS. 8–9, taken along lines X—X, XI—XI and XII, respectively, in FIG. 9, FIG. 13 a longitudinal section of the ostomy rod of FIG. 8 in the bent state, FIG. 14 a third embodiment of the ostomy rod, seen from above, FIG. 15 a longitudinal section, analogous to FIG. 9, of the embodiment of FIG. 14, FIGS. 16–18 cross sections of the rod of FIGS. 14–15, taken along lines XVI, XVII and XVIII, respectively, in FIG. 15, and FIG. 19 a perspective view of the rod of FIGS. 14–17, positioned on a bandage and a first annular coupling member, under a bowel loop.

The ostomy equipment shown in FIG. 1 consists of a bandage 10; an ostomy bag 12 with a rear wall 14 facing the bandage 10 and a front wall 16; and a ring coupling consisting of two annular coupling rings, a first coupling member 18 (which hereinafter will also be called a plate coupling) connected to bandage 10, and a second coupling member 20 (which hereinafter will also be called a bag coupling) connected to bag 12. The ring coupling is normally circular but may have other shapes, e.g. oval or polygonal with rounded corners.

The bandage is a skin-friendly adhesive skin barrier, in this embodiment of the kind described in U.S. Pat. No. 4,231,369. At the side facing the skin of the patient it has a layer of adhesive material and at the side facing the plate coupling a non-adhesive, flexible, impervious film, e.g. of EVA (ethylene-vinyl acetate) copolymer. The bandage may be of another kind, e.g. a pad of an elastic plastic material, e.g. a foam plastic, or a conventional bandaging material.

Bandage 10 is provided with an opening 22. The ostomy usually projects through a central opening in coupling members 18,20 and into bag 12. Preferably opening 22 is so adjusted to the size and shape of the ostomy that the perimeter 24 in use abuts the ostomy.

Bag 12 consists of an impervious plastic sheet material and its two walls are united at the edges in conventional manner, e.g. by heat sealing. The bag may be of any known construction and does not in itself constitute any part of the invention. It has an inlet opening 26 for fecal material.

Ring coupling 18,20 consists of a plastic material which is sufficiently elastic to yield to a limited degree to forces exerted when the two coupling members are to be brought into or out of engagement with each other. Suitable materials are, e.g., EVA copolymer and LLDPE (linear low density polyethylene), but also polyethylene or polypropylene may be used. The coupling members are profiled so as to have co-operating annular faces to tighten against escape of fluid and solids when the members are in engagement, and co-operating engaging faces to safeguard against intentional release of the coupled state of the two members, as will presently be explained.

In the embodiment shown the plate coupling is constructed as a profiled member having a generally cylindrical body portion 28 with a generally U-shaped cross-section, the opening of the U facing bandage 10. This serves to stiffen the ring against torsion out of a plane parallel with the bandage but is not essential since the body portion 28 might also be solid. At the side of the body portion 28 facing the bandage (its under side) it is provided with two annular flanges 30,32 which are plane-parallel with bandage 10 and of which at least one, here flange 30, is firmly connected to the bandage, e.g. by adhesion or heat sealing as intimated by reference numeral 34.

At the end opposite flange 32 body portion 28 has a radially outwardly extending annular projection 36 provided at its under side with an engaging surface 38 facing flange 32 and substantially plane-parallel therewith. In the radially outermost part of projection 36 is an annular rim 40. At the radially inner side body portion 28 has a substantially frusto-conical surface 44 the smaller diameter of which is adjacent flange 30.

The other annular coupling member 20, the bag coupling, has a body portion 50 which in proximity to the end thereof which extends away from bag 12 is provided with a radially inwardly extending projection 52 with an engaging surface 54 facing the bag In the coupled state of ring coupling 18,20 the surface 54 is substantially parallel with bandage 10. However, in the coupled state engaging surfaces 38,54 are preferably not completely parallel but diverge a little, e.g. 5°–10°, in the radially inward direction. Thereby one avoids a pumping effect due to small movements of the two annular members relative to each other, e.g. caused by movements of the patient. Engaging surface 54 is a little narrower than engaging surface 38, which ensures that rim 40 gives an almost linear (circular when the rings are circular) tightening surface by engaging body portion 50 in the angle between the same and the surface 54 on projection 52. This angle is preferably about 90°.

Figure 3:
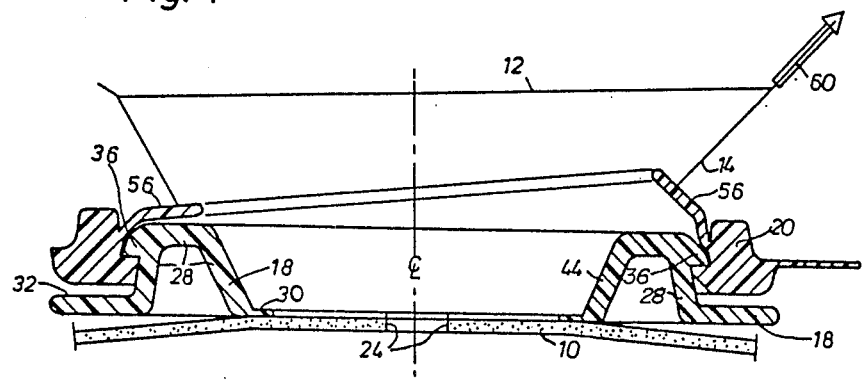
Figure 2:
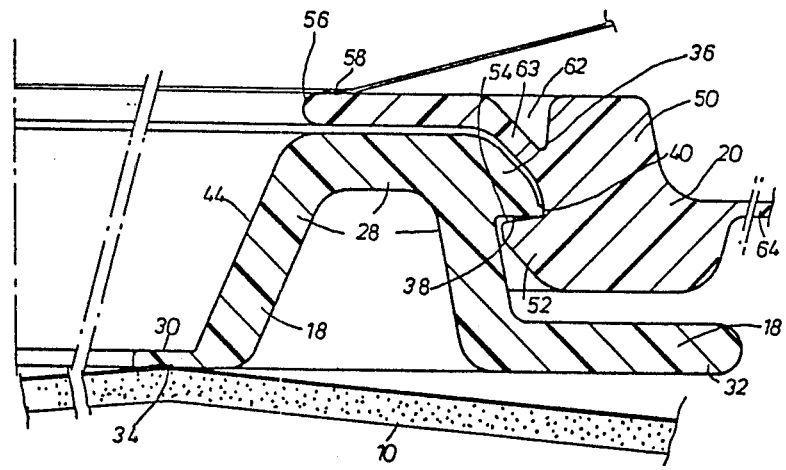

Body portion 50 in the end farthest away from bandage 10 (in the coupled state of the equipment) has a radially inwardly extending projection 56 which in the embodiment shown in FIGS. 1–3 is much wider than engaging surfaces 38 and 54. In an area 58, the parts of bag 12 adjacent its inlet opening 26 are adhesively, by heat sealing or in other tightening manner, connected to projection 56. Area 58 constitutes an annular connecting field which in its entirety is situated radially within the tightening surface between rim 40 and the angle between projection 52 and body part 50, and also in its entirety radially within the engaging faces 38,54. As schematically shown in FIG. 3 it is hereby obtained that a one-sided pull in bag 12, visualized by an arrow 60, will not tend to cause leakage in the almost linear tightening surface or put projections 36,52 with their engaging surfaces out of engagement. Such a pull will bend flange 56 in and near its site of attack and will not be transferred to body portion 20 in the same side of the ring but, on the contrary to body portion 20 in the opposite side of the bag coupling. Here it will cause the engagement between engaging and tightening surfaces to be strengthened.

Between projection 56 and body portion 50 there is a groove 62 defining an oblique elongation 63 of projection 56, and this elongation has smaller thickness of material than the remainder of projection 56. Upon an oblique or uneven pull, the bending of the flange takes place at the thinner elongation 63, which strengthens the effect just described.

It is observed that the one-sided pulling forces which in practice would tend to cause unintentional local opening of the coupling at most will be a few kilograms, determined mainly by the contents of the bag. The coupling is not resistant to strong pulling forces, e.g. of 10 kg or more, because then it would be too difficult to bring it into or out of engagement. To facilitate the opening of the coupling the bag coupling may in known manner be provided with a flap 64.

Figure 4:
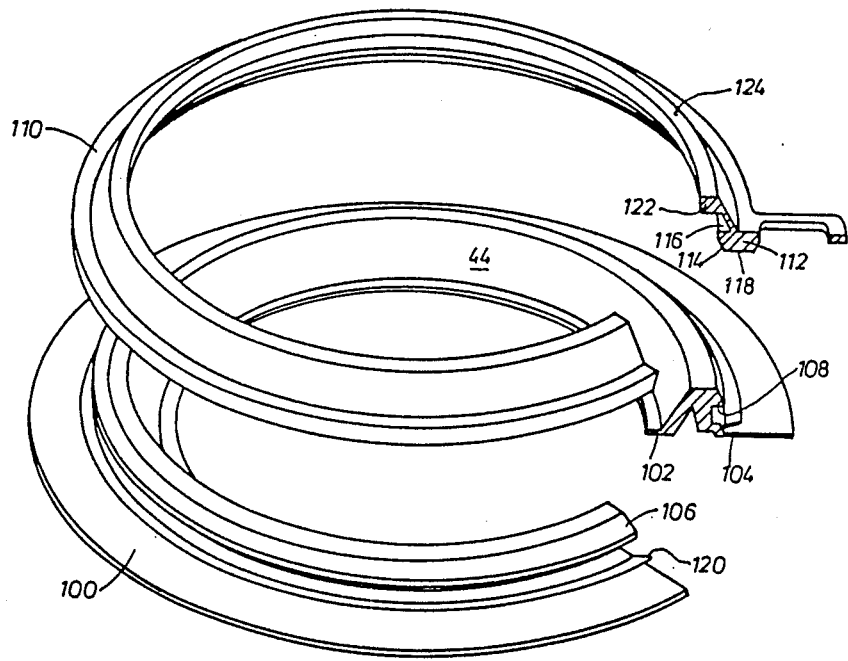

In the embodiment shown in FIG. 4 a plate coupling 100 is provided with two annular flanges 102,104 and a bandage (not shown) can be attached to flange 102. A substantially axial body portion projects from flanges 102–104 and is provided with an inner frusto-conical surface 44 and a radially outwardly extending projection 106 having an engaging surface 108 facing flange 104. A bag coupling 110 has a body portion 112 with a radially inwardly extending projection 114 provided with an engaging surface 116 which in this embodiment is planeparallel with surface 108 when the plate coupling and the bag coupling are in engagement. Plate coupling 100 is provided with a radially outwardly extending thin annular tightening flap 120 which in the coupled state is in tightening engagement with a surface 118 on body portion 112. Bag coupling 110 in its end farthest away from surface 118 has a radially inwardly extending projection 122, adapted to carry an ostomy bag (not shown). The connecting area between the bag and projection 122 is an annular, plane surface limited in its radially outer part of a line visualized by reference numeral 124 and in the radially inner part of the inner edge of projection 122. Line 124 is radially inside the engaging surfaces 108,116 and the tightening surface between the annular flap 120 and the annular surface 118.

Figure 5:
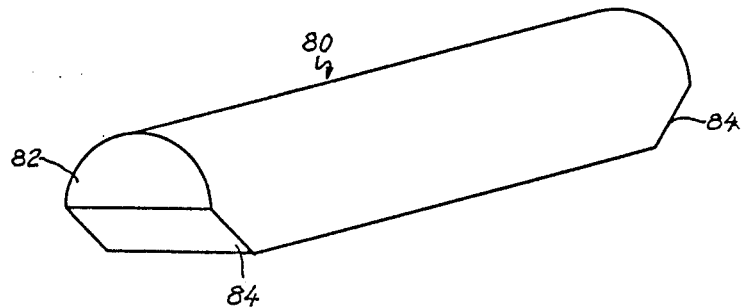

An ostomy rod 80 shown in FIG. 5 is solid and trapeziform yet rounded at the upper side (i.e. the side adapted to be turned away from the bandage) so that the cross-section here is semicircular. Rod 80 may be rigid or flexible, e.g. elastically bendable and might also have oval, semioval or circular cross-section.

The semicircular part of the cross-section of rod 80 is perpendicularly cut at the ends so as to form semicircular end faces 82 but the end faces might also have other shapes.

The lower part, i.e. the part of the rod adapted to be adjacent the bandage when in use, is bevelled to form oblique faces 84 converging towards the lower part of the rod. Faces 84 preferably are plane as shown, but may be parts of a conical surface. The angle between the under side of rod 80 and oblique faces 84 in the embodiment shown is about 120°.

Figure 6:
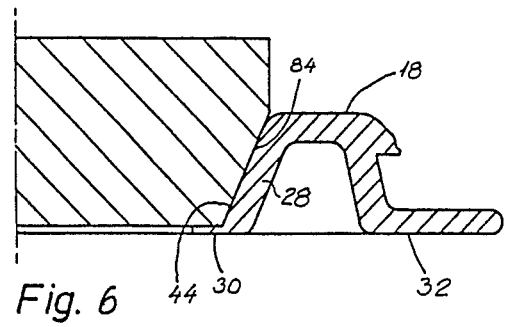

Oblique faces 84 are adapted to co-operate with the frusto-conical surface 44 on the plate couplings 18 shown in FIGS. 1-4, as is most clearly seen in FIG. 6.

Figure 7:
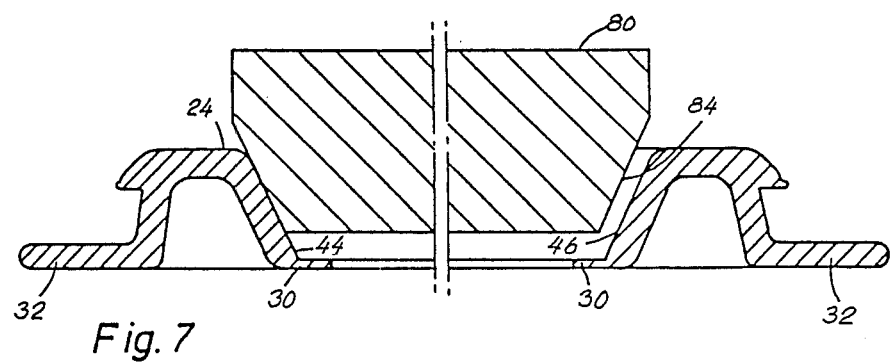
Figure 8:
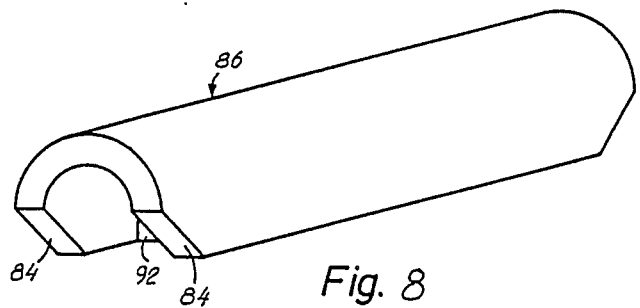

The ostomy rod 80 is adapted to be placed under a bowel loop to prevent it form sliding back into the abdominal cavity; when the rod has been positioned under the bowel loop and the plate coupling 18 has been positioned the oblique faces 84 on the rod are to be placed in engagement with the frusto-conical surface 44 on plate coupling 18. If in this operation one end of the rod becomes situated radially a little too far from the middle of the coupling ring, the rod nevertheless may enter its correct position because as illustrated in FIG. 7 the oblique faces 84 may slide on the frustoconical surface 44. The angular orientation relative to the periphery is unimportant.

An expedient length of the rod is 6–12 cm, e.g. about 10 cm, and the coupling ring member 18 has a corresponding inner diameter.

The ostomy rod 86 shown in FIGS. 8-13 in its outer appearance much resembles that shown in FIG. 5 but differs therefrom in having an inverse U-shaped cross-section as is clearly seen in FIGS. 8 and 11-13. Its upper, curved part 87 (which might be flat) is called the connecting part of the U and the two parts 88 projecting therefrom (and which may be parallel, diverging or converging) are called the branches.

Figure 9:
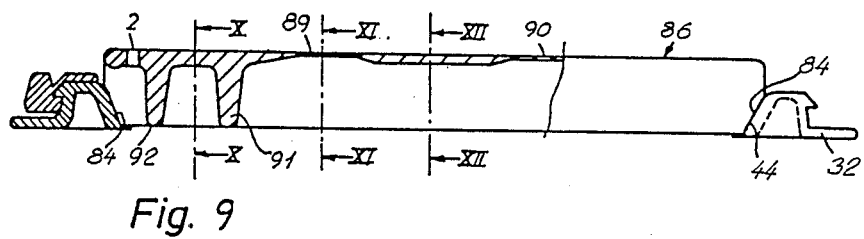
Figures 10, 11, 12:
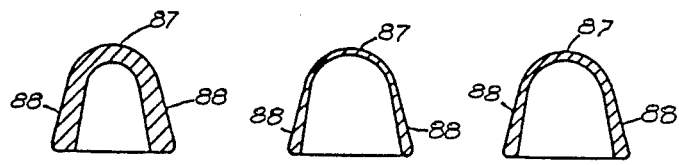

From FIG. 9 it is seen that two zones 89,90, one at each side of the transversal middle plane (which is the plane represented by line XII—XII), of the rod have smaller thickness of the material than the remainder of the rod. The decreased material thickness does not apply only to the connecting part 87 but also to the branches 88 as seen from FIG. 11. The decreased thickness of material has the effect that the rod is weakened against bending influences in these two zones. The distance between zones 89,90 is approximately as the width of a bowel section which after a surgical operation in the abdominal cavity has been pulled outside it and it is typically 2-3 cm.

Figure 13:
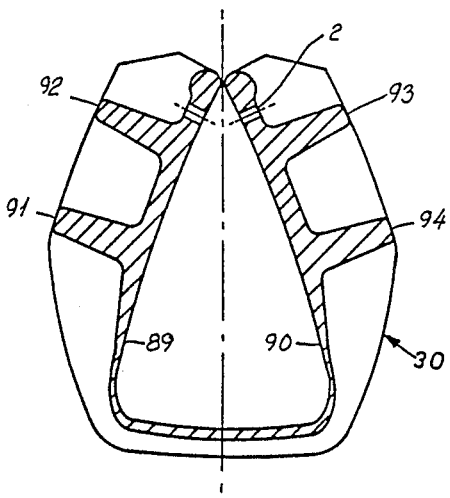
Figure 14:
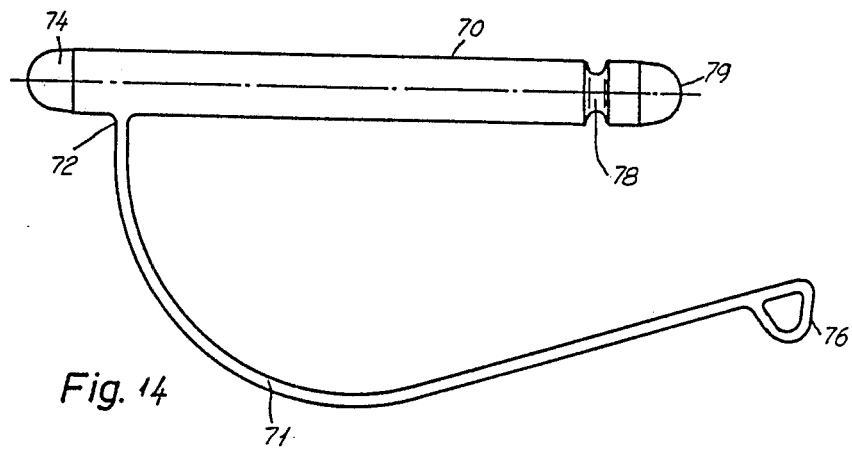

The decreased thickness of material and reduced resistance against bending makes it possible to bend the ostomy rod 86 so that its end come close to each other as shown in FIG. 13. The rod is maintained in this state during positioning and change of bandages and plate coupling to be placed under the rod, between its "open" bottom and the skin of the patient; it is hereby possible to position and remove a bandage without reciprocating the rod and without risk of infecting the abdominal cavity or of causing discomfort for the patient. During these operations the ends of the rod are kept in position with its end close to each other by means of the fingers, a pean or a double hook (not shown) which, e.g., may be caused to engage in only partly shown holes 2 near the end of the rod, or by means of string through holes 2, or in other manner.

To increase the rigidity of the rod outside zones 89,90 it may be provided with internal stiffening ribs or preferably as shown with transversal internal plates firmly connected with the inner side of the U. In the embodiment shown in FIGS. 8-13 there are four such plates, viz. plates 91,92 near one end and plates 93,94 near the other end of the rod; there might also be one or more such plates between weakened zones 89,90.

The rod 86 is bevelled in both ends to form oblique faces 84, adapted to engage the frusto-conical surface on plate ring 18, so as to keep the rod in position.

An ostomy rod 70 of the embodiment shown in FIGS. 14-19 also has zones 89,90 of reduced material thickness at each side of its transversal middle plane. The reduced material thickness applies, as is seen from FIG. 18, both to the connecting part 87 and the branches 88. In this embodiment there are three transversal stiffening plates, viz. plates 92 and 93 near the ends of the rod and a plate in the transversal middle plane of the rod. This embodiment also has oblique faces 84 to co-operate with the frustoconical surface 44 on the first coupling member, i.e. plate coupling 18. In FIG. 19 it is seen that the plate coupling 18 has flanges 30,32 suitably connected with a bandage 10, e.g. a skin barrier. When ostomy rod 70 is in position under a bowel loop 96 as shown in FIG. 19, oblique faces 84 engage the frusto-conical surface 44, and moreover the under side, i.e. the free ends of the branches of the U are resting on bandage 10.

Figure 15:
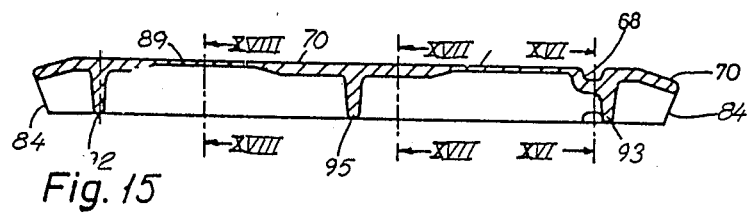

The embodiment of FIGS. 14-19 especially differs from that of FIG. 8-13 by being provided with a safety means in the form of a flexible string 71 which in one end 72 is firmly connected, possibly integral with rod 70 near one end 74 thereof. String 71 in its other end is provided with an eye 76 adapted to engage in a groove 78 near the other end 79 of the rod 70. When the rod is to be positioned under the bowel loop 96, eye 76 is not in engagement in groove 78 and the rod is put with the end 79 leading under the bowel loop. Thereafter string 71 is led outwardly of the bowel loop and over the rod end 79, which for this purpose is sligthly bevelled even at the upper side as is seen in FIGS. 15 and 19, and is finally caused to slip into groove 78 whereby eye 76 and groove 78 together act as a kind of lock. This ensures completely that rod 70 cannot unintentionally leave its position under the bowel loop. When a bandage such as bandage 10 with plate coupling 18 is to be positioned on the skin of the patient just outside the ostomy opening through which the bowel loop 96 is projecting, the ends of rod 70 are bent to a configuration like that shown in FIG. 13 and is maintained in that configuration until bandage and ring are in the correct position. Thereupon the rod is returned to its normal configuration with the oblique faces 84 in engagement on the frusto-conical surface 44 and the under side resting on bandage 10 and flange 30.

A lot of other constructions of the rod are possible. Thus, it may be solid and made of an elastic material such as a synthetic or natural rubber. It may have semicircular or semielliptic cross-section with the flat surface being the under side of the rod. The bending of such a rod may be facilitated if one or two portions of the curved surface is (are) cut away to define one or two flat surfaces parallel with the lower flat surface of the rod, and hence one or two zones with improved ability of being bent, said zone(s) being placed symmetrically with respect to the transversal middle plane of the rod. Instead of forming a flat upper surface in this manner, there might be cut a groove from the upper, curved surface, such groove representing, e.g., ⅓ of the cross-sectional area of the rod, and extending to near the under side of the rod and longitudinally extending symmetrically with respect to the transverse middle plane of the rod, e.g. over altogether about half of its length.

I claim:

1. An ostomy equipment comprising in combustion
   (a) a substantially flat bandage adapted to be adhesively affixed to the wearer's abdomen around an intestinal opening, and
   (b) a two-part ring couples adapted to releasably attach an ostomy bag to the bandage, wherein the ring coupling comprises
      (i) a first coupling ring comprising a flat bandage connection flange firmly connected to the bandage, and a generally cylindrical body portion projecting axially outward from the flange, and
      (ii) a second coupling ring comprising an axially oriented body portion generally adjacent to and radially outside said body portion of said first coupling ring;
   said second coupling ring having a flat bag sealing flange projecting radially inwardly, from an axially outward portion of said second coupling ring, said bag sealing flange being firmly connected to the bag by means of a sealed annular connection surface, and
   said body of said first and second coupling rings having respective co-operating annular tightening engaging faces which are generally parallel with the flat bandage connection flange of the first coupling ring;
   wherein the annular connection surface where the bag and the bag sealing flange of the second coupling ring are connected is, in its entirety, situated radially within the annular co-operating tightening engaging faces of the respective coupling rings; and
   wherein said bag sealing flange of the second coupling member has the form of an annular flexible flange, the connection surface at which the bag and the second coupling ring are affixed being at a radially innermost and axially outermost part of said flange.

2. The ostomy equipment claimed in claim 1, wherein the annular bag sealing flange to which the bag is affixed is substantially wider, measured radially, than the engaging faces on the co-operating projections.

3. The ostomy equipment claimed in any one of claims 1-2, in which the engaging face of the first coupling ring co-operating with the engaging face of the second coupling ring extends radially outwardly relative to the body portion of said first coupling ring, and the corresponding engaging face of the second coupling ring is directed radially inwardly relative to the body portion thereof, and
   wherein a radially outermost portion of said first coupling ring is provided with an annular rim adapted to tightening engagement in an angle defined between the radially inwardly extending engaging face of the second coupling ring and its body portion.

4. The ostomy equipment claimed in claim 2, wherein the inwardly directed bag sealing flange to which the bag is affixed is flexible so as to flex axially outward under a force having an axially outward component.

5. The ostomy equipment claimed in claim 4, wherein bag sealing flange is flexible radially and axially outward under a radially and axially outward force, such that under the effect of such force, such force is transferred by the bag to remote portions of said co-operating engaging faces generally away from the direction of such force, whereby said remote portions tighten for preventing the escape therethrough of gases, liquids, and solids.

6. The ostomy equipment claimed in claim 5, wherein an annular groove is formed in said bag sealing flange radially outwardly of said connecting surface for enhancing the flexibility of the flange.

* * * * *